United States Patent [19]

Madaus et al.

[11] Patent Number: 4,871,763

[45] Date of Patent: Oct. 3, 1989

[54] METHOD OF TREATING LIVER DISEASES USING PURE SILIBININ

[75] Inventors: Rolf Madaus, Cologne; Klaus Görler, Bergisch Gladbach; Hartwig Soicke, Cologne, all of Fed. Rep. of Germany

[73] Assignee: Dr. Madaus GmbH & Co., Cologne, Fed. Rep. of Germany

[21] Appl. No.: 171,176

[22] Filed: Mar. 18, 1988

Related U.S. Application Data

[63] Continuation of Ser. No. 800,052, Nov. 20, 1985, abandoned.

[30] Foreign Application Priority Data

Nov. 22, 1984 [DE] Fed. Rep. of Germany ....... 3442641
Oct. 23, 1985 [DE] Fed. Rep. of Germany ....... 3537656

[51] Int. Cl.[4] ............................................ A61K 31/335
[52] U.S. Cl. .................................... 514/45.2; 549/362
[58] Field of Search ......................... 549/362; 514/452

[56] References Cited

U.S. PATENT DOCUMENTS 3,773,932 11/1973 Madaus ............................ 424/185.1

OTHER PUBLICATIONS

Wagner et al., Arzneim Forsch, 24(4), 466-471 (1974).

Primary Examiner—Nicky Chan
Attorney, Agent, or Firm—Felfe & Lynch

[57] ABSTRACT

The present invention provides a process for the preparation of substantially pure silibinin from the fruit of *Silybum marianum*, as well as pharmaceutical compositions containing it for the treatment of diseases of the liver.

2 Claims, No Drawings

METHOD OF TREATING LIVER DISEASES USING PURE SILIBININ

This application is a continuation of application Ser. No. 800,052, filed Nov. 20, 1985, now abandoned.

FIELD OF THE INVENTION

The present invention is concerned with a process for the preparation of isosilybin-free silibinin and with pharmaceutical compositions containing it.

BACKGROUND AND PRIOR ART

Lady's thistle (Silbum marianum (L) Gaertn. (Carduus marianus L.) has long been knwon as a medicinal plant. From the flavolignans occurring in the fruits of this plant, R. Munster isolated a component called silybin (f. Dissertation R. Munster, Munchen, 1966). The chemical structure of this compound was elucidated by A. Pelter and R. Hansel (cf. Tetrahedron Letters, London 25 2911-2916/1968).

It is known that silybin, previously also called silymarin I, is a valuable liver therapeutic substance (cf. Federal Republic of Germany Patent Specification No. 17 67 666). A technical process for the preparation of silybin (silymarin I) is described, for example, in Federal Republic of Germany Patent Specification No. 19 23 082.

As long ago as 1974, H. Wagner, P. Diesel and M. Seitz (Arzneimittelforschung, 24 (4), 466-471) assumed, with regard to silybin, two positional isomers, namely, silybin and isosilybin. This conjecture was investigated and experimentally confirmed by A. Arnone, L. Merlini and A. Zanarotti (J. Chem. Soc., Chem. Comm., 16 696-697/1979). According to this, the known silybin consists of two different compounds, namely the compounds of the following structural formulae A and B:

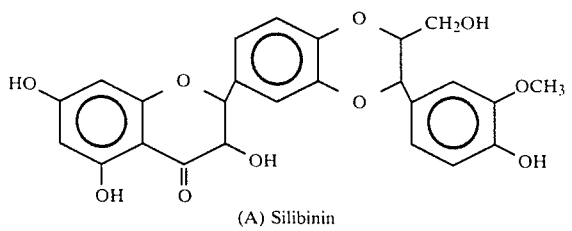

(A) Silibinin

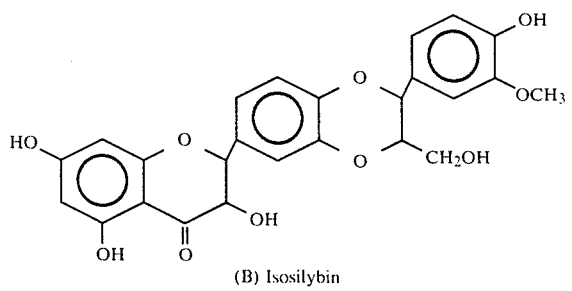

(B) Isosilybin

From these structural formulae, it can be seen that these compounds are positional isomers. The compound of formula A has recently been given the INN designation silibinin. This designation is also used herein for the compound of formula A.

The two-above mentioned compounds A and B have hitherto only been separated and prepared in analytical amounts and nothing is known about the pharmacological actions of the individual isomers.

In order to study the properties of these two isomers, it was necessary to have available purified quantities of each. In order to obtain this a method was developed whereby silybinin is prepared which is free of isosilybin.

Hence it is an object of this invention to provide a process for the preparation of isosilybin-free silibinin.

Once this pure silybinin was obtained, studies thereupon show that pure silibinin possesses useful pharmaceutical properties.

Hence it is a further object of this invention to obtain the pharmaceutically useful compound silybinin, and compositions containing this compound.

How these and other objects of the invention are accomplished will be seen from the Detailed Description of the Preferred Embodiments which now follows.

DETAILED DESCRIPTION OF PREFERRED EMBODIMENTS

I. Obtaiing a Silymarin Mixture

A method for obtaining silymarin, which is a mixture of related compounds, is disclosed in U.S. Pat. No. 4,368,195, assigned to the assignee of record of this application. This method is used to extract the mixture of silybinin and isosilibinin used herein, with some modifications. Briefly, dried fruit of *Silybum marianum L. Gaertn.* is freed from the bulk of fatty oil present therein by bursting open the fruit by high mechanical pressure. The dried fruit residue contains a residual oil content of 5-10%. This residual is extracted with ethyl acetate, and, after the ethyl acetate is removed, it is evaporated leaving behind a dry residue. This residue is then dissolved in 2% by weight of a two phase solvent, where the lower phase solvent is methanol and water and the upper phase is a mixture of methanol, water, and petroleum ether (95:5:100, boiling point approx. 40°-60° C.). Following solvation, the mixture is centrifuged until clear, to remove flocculent solid materials. The remaining dry residue is subjected in the solvent system to multiplicative, uniform partitioning in countercurrent wherein the total flowing volume ratio of the upper phase/lower phase remains in a 1:1 ratio. Subsequently, the lower phase is allowed to flow off, and is evaporated to dryness to obtain a 70-80% polyhydroxphenyl-chromanone mixture, which contains silymarin I-IV. This is a brownish powder, and it is from this powder that the silibinin is separated from the isosilybinin.

II. Separating Silybinin from Silymarin Mixture—Method A

The brownish powder obtained supra is suspended in 3-5 times its own weight of methanol. This suspension is heated to the boiling point while stirring. Following this, from ⅓ to about ⅔ of the methanol is removed under reduced pressure, leaving behind a concentrate. The concentrate is left to stand at ambient temperature, which results in the formation of a precipitate settling out of the concentrate. The precipitant is washed, 1-3 times, with methanol, followed by drying of the methanol. The precipitate is then dissolved, while heating in ethyl acetate (40-60 times the weight of precipitant), and is treated with active charcoal under reflux conditions. The charcoal is filtered off, and the filtrate is evaporated, under reduced pressure, to about 1/10 of its original volume. This forms a concentrate which is mixed with about 10/10 of its volume of methanol. This mixture of concentrate and methanol is allowed to stand for several hours at ambient temperature, before stirring and removal of the precipitate product which remains. This precipitate product, which is substantially pure silybinin, is washed 1-3 times with ethyl acetate, and is then dried in a vacuum.

III. Separating Silybinin from Silymarin Mixture—Method B

In this method, a silymarin mixture as described in I, supra is used as starting material. One part by weight of the mixture is suspended in water saturated ethyl acetate (0.7-1.5:8 v/v) and this is allowed to stand for 1-2 days, while a precipitate forms. This precipitate is filtered off, and is washed with cold water saturated ehtyl acetate (0.7 to 0.15 parts by weight) and is dried in a vacuum at 30°-50° C. The resulting product is dissolved in 30-50 parts by weight of dry ehtyl acetate at is boiling point, and is refluxed for two hours with 0.2 to 0.4 parts by weight activated charcoal. The charcoal is removed, and the filtrate concentrated in a vacuum at 30°-50° C. Water saturated ethyl acetate is added to the resulting concentrate, and, after about 5-10 hours, the precipitate, which is pure silibinin, is filtered off and suspended in 0.9 to 1.5 parts by weight ehtyl acetate. This suspension is predried vacuum, 30°-50° C.), ground, and dried again (vacuum, 30°-50° C.).

What will be evident to one skilled in the art is that, according to the description given supra, a general two-step process takes place. In the first step, i.e., treatment of crude silymarin with water saturated ethyl acetate, silymarins II through IV are removed, together with 20-30% other materials in the mixture, together with a portion of the isosilybin. Thus, crude silibinin is obtained with a yield of about 80-85% based upon the crude silymarin used. This crude silibinin is about 80-84% of the desired product. Note that crude silibinin is found, in the art, to be a mixture of isosilybin and silibinin in a ratio of about 1:4. Hence, the first step has already produced a more pure product than is taught from the art.

In the second step the product of step I is treated with various washings of ethyl acetate. This removes the remaining isosilibin and other residues from the desired silibinin.

Unique to this process is the use of only ethyl acetate, but with different water contents. Hence, after the precipitate has been washed with the cold, water saturated ethyl acetate, if more highly purified silybinin is desired, it is necessary that dry ethyl acetate be used, followed by water saturated ethyl acetate. In this way, a silybinin extract which is about 96-98% pure, is obtained.

According to a preferred embodiment of the process according to the present invention, (a) one part by weight of the brownish powder is suspended in 0.9 parts by weight of water-saturated ethyl acetate, left to stand at ambient temperature for 48 hours and the precipitate obtained filtered off with suction, (b) the precipitate is washed with 0.09 parts by weight of cold, water-saturated ethyl acetate and dried in a vacuum for 48 hours at 40° C., (c) the product obtained is dissolved in 36 parts by weight of dry ethyl acetate at the boiling temperature thereof, heated under reflux for 2 hours with 0.36 parts by weight of active charcoal, filtered and concentrated at 50° C. in a vacuum to a total volume of 3.33 litres, (d) 0.6 parts by weight of water-saturated ethyl acetate is added to the concentrate at ambient temperature, left to stand for 12 hours at ambient temperature and the precipitated product filtered off and e) this product is suspended twice in, in each case, 1.8 parts by weight of technical grade ethyl acetate and filtered, predried in a vacuum at 40° C. for24 hours, ground and further dried in a vacuum for 48 hours at 40° C.

It has been found that isosilybin-free silibinin is very suitable for pharmaceutical purposes. Surprisingly, we have found that it has considerable advantages in comparision with other known components of *Silybum marianum* extracts. It is especially suitable for the treatment of liver cirrhosis and toxic-metabolic liver damage. It can also be used prophylactically so that the mentioned damage does not even occur.

Consequently, the present invention also provides a pharmaceutical composition which contains silibinin, in admixture with a solid or liquid pharmaceutical diluent or carried. These compositions are usually employed systemically, for example in the form of pills, capsules and solutions, together with conventional carriers.

The daily dosage for an adult human is usually about 50 to 500 mg., depending upon the state of the patient and the severity of the symptoms of the disease.

The following Examples are given for the purpose of illustrating the preparation of isosilybin-free silibinin by the process according to the present invention:

EXAMPLE 1

500 g. of a polyhydroxy-phenylchromanone mixture (Silymarin I-IV = Silymarin I-IV group; content about 70%) obtained according to Federal Republic of Germany Patent Specification No. 19 23 082 (see column 8, lines 14-19), are suspended in 2 kg. of methanol (about 2.53 litres) and heated to the boil for 15 minutes, while stirring. After this time, some silibinin can already precipitate out of the solution thus obtained. Subsequently, 0.75 to 1.25 kg. (about 0.96 to 1.58 litres) of methanol are removed in a vacuum and the residue is left to stand at ambient temperature for 10 to 28 days. The precipitated silibinin is filtered off and then washed twice with 50 ml. amounts of cold methanol. After drying at 40 C. in a vacuum, the isolated crude silibinin is further purified as follows: 60 g. crude silibinin are dissolved, with heating, in 3 litres of technical grade ethyl acetate, subsequently mixed with 20 g active charcoal and further stirred for 2 hours under reflux conditions. Thereafter, the solution is clarified by filtration and the solution evaporated at 50° C. under reduced pressure to about 250 ml. The concentrate is stirred for 15 minutes with the use of an Ultra-Turrax apparatus and, while stirring, mixed with 25 ml. of methanol. Subsequently, the mixture is left to stand overnight at ambient temperature. Before filtering off with suction the precipitated silybin, the solution is stirred again for 5 minutes with an Ultra-Turrax apparatus. The suction filtered precipitate is then washed twice with 50 ml. amounts of ethyl acetate and dried in a vacuum drying cabinet overnight at 40° C. The product is subsequently ground and further dried under the same conditions for 48 hours.

EXAMPLE 2

1 kg of the polyhydroxyphenylchromanone mixture used as starting material in Example 1 is suspended in 1 litre of water-saturated ethyl acetate, using a Turrax stirrer. After standing for 48 hours at ambient temperature, the precipitate is filtered off with suction, washed with 100 ml of cold, water-saturated ethyl acetate and dried in a vacuum at 40 C for 48 hours. The yield of this intermediate product, i.e. crude silibinin, is, depending upon the quality of the crude silymarin used, 80 to 85%, referred to the silibinin content in the crude silymarin, with a content of from 80 to 84%.

The crude silibinin thus obtained is dissolved in 40 litres of dry ethyl acetate at the boiling temperature thereof, boiled under reflux for 2 hours with 360 g. active charcoal, filtered and concentrated in a vacuum at 50 C. to a total volume of 3330 ml. 667 ml. of water saturated ethyl acetate are added to this solution at ambient temperature, with intensive stirring. 1 to 3 hours thereafter, the crystallisation of the silibinin commences. After standing overnight, the precipitated silibinin is separated by filtration, suspended twice for 5 to 10 minutes in, in each case, 1200 ml technical grade ethyl acetate, again filtered and predried in a vacuum at 40° C. for 24 hours. After grinding, it is further dried in a vacuum for 48 hours at 40° C. The yield of silibinin, referred to the silibinin content of the crude silibinin, is 79 to 85%, with a content of 96 to 98.5% silibinin, depending upon the quality of the crude silibinin.

Clinical experiments with silibinin

In recent decades, toxic liver damage has increased very considerably. As ever, the commonest cause of damage is alcohol.

By means of controlled studies, it was possible to demonstrate the superiority of silibinin in comparison with a placebo or other comparative therapies. In a double blind study, 66 patients with alcohol-toxic liver damage were used for a randomised study using silibinin (n=31) against placebo (n=35).

The statistically evaluated results showed that silibinin is significantly superior to the placebo, the substantially shorter healing times in comparison with the placebo thereby being noticeable. In a second blind study with 76 patients, 39 of which received silibinin and 37 of which received a control therapy, the differences in favour of silibinin were highly significant.

In the case of liver-toxic effects of narcosis in connections with operations on the abdominal organs, it could be demonstrated that the pre-operative administration of silibinin significantly reduced the post-operative increase of the liver enzymes in the blood. Liver damage induced today ever more frequently due to certain medicaments is also effectively prevented by silibinin. This could be shown, for example, in the case of a phenylhydantoin-induced hepatosis in which, in spite of further prescription of the essential cramp-preventing medicament, in the case of the simultaneous administration of silibinin, all laboratory values normalised within a very short period of time.

Further investigations in the case of patients with schizophrenias and severe liver damage due to the prescription of chlorpromazine also demonstrated the positive action of silibinin. Other experiments were concerned with the prevention of liver-damaging effects of, for example, chloroquine and asparaginase. In the case of all liver damage caused by occupational factors, in the case of all treated patients, the pathologically increased laboratory findings could be substantially improved, independently of the particular cause of possible additional diseases.

Furthermore, there is sufficient evidence that silibinin also brings about substantial improvements in the case of chronic-inflammatory liver diseases. For example, patients with liver cirrhosis were taken into a prolonged study in a randomised double blind trial in which silibinin was tested against a placebo. The criterion for the evaluation of the therapeutic success was, in particular, the survival times. A clear superiority of silibinin in comparison with the placebo treatment was here shown.

A comparison of action between silibinin, isosilybin and silybin (silibinin/isosilybin mixture), using the model of phalloidin and praseodymium intoxication in mice after intravenous administration, was carried out.

The anti-hepatotoxic action of silibinin, isosilybin and silybin in the form of N-methylglucamine salts was tested to dosages of 50 and 100 mg./kg$^{-1}$, referred to silibinin, using as a model the phalloidin and praseodymium poisoning of mice after intravenous administration. The administration of the test substance took place 1 hour before the phalloidin and 1 hour before and 6, 24 and 48 hours after the praseodymium. In the case of phalloidin poisoning, the survival rate was evaluated and, in the case of the praseodymium poisoning, various serum and liver parameters were evaluated 72 hours after intoxication.

In the case of phalloidin intoxication, the survival rate after the administration of silibinin at both dosage levels was 100%, whereas with the other tested substances, the survival rate of 40% in the case of the untreated, damaged controls was not exceeded.

Isosilybin proved to be incompatible in connection with the praseodymium intoxication so that the dosage of 100 mg./kg$^{-1}$ had to be divided up into two partial administrations.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A method of treating liver cirrhosis or toxic-metabolic liver damage comprising administering to a patient a therapeutically effective amount of substantially pure silibinin.

2. A method as in claim 1, wherein said silibinin is administered in an amount ranging from about 50 mg to about 500 mg per day.

* * * * *